United States Patent [19]
Manley

[11] Patent Number: 5,574,049
[45] Date of Patent: Nov. 12, 1996

[54] 2,2-DIALKYL- AND 2,2-DIALKYL-3,4-DIHYDRO-3-HYDROXY-2H-1-BENZOPYRANS

[75] Inventor: Paul W. Manley, Basel, Switzerland

[73] Assignee: Sandoz Ltd., Basel, Switzerland

[21] Appl. No.: 470,667

[22] Filed: Jun. 6, 1995

Related U.S. Application Data

[63] Continuation of Ser. No. 256,803, filed as PCT/EP92/02719, Nov. 25, 1992, abandoned.

[51] Int. Cl.$^6$ .................... A61K 31/44; C07D 407/14
[52] U.S. Cl. .................... 514/383; 514/318; 514/337; 514/218; 514/339; 514/309; 546/256; 546/194; 546/278.4; 546/141; 546/257; 546/277.1; 546/13; 546/282.7; 546/283.1; 540/524
[58] Field of Search .................... 506/256; 514/333

[56] References Cited

FOREIGN PATENT DOCUMENTS

| | | |
|---|---|---|
| 126311 | 11/1984 | European Pat. Off. . |
| 139992 | 5/1985 | European Pat. Off. . |
| 250077 | 12/1987 | European Pat. Off. . |
| 346724 | 12/1989 | European Pat. Off. . |
| 488301 | 6/1992 | European Pat. Off. . |
| 561357 | 9/1993 | European Pat. Off. . |
| 4004268 | 8/1991 | Germany . |
| 9413656 | 6/1994 | WIPO . |
| 9413657 | 6/1994 | WIPO . |
| 9412173 | 6/1994 | WIPO . |
| 9414799 | 7/1994 | WIPO . |

OTHER PUBLICATIONS

J. Med. Chem., vol. 33, No. 2, pp. 492–504 (1990).

*Primary Examiner*—Jane Fan
*Attorney, Agent, or Firm*—Robert S. Honor; Melvyn M. Kassenoff; Joseph J. Borovian

[57] ABSTRACT

2,2-di($C_{1-5}$alkyl)- and trans-2,2-di($C_{1-5}$alkyl)-3,4-dihydro-3-hydroxy-6-(pyridin-4-yl)-2H-1-benzopyrans, e.g. of formula

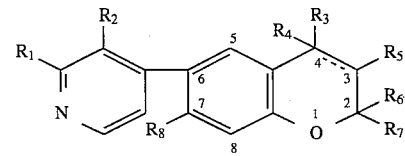

in which $R_1$ and $R_2$=H, alkyl, hydroxyalkyl or alkoxyalkyl, at least one being other than H, $R_3$=typically a 2-piperidinone group, $R_4$=H and $R_5$=—OH or $R_4$+$R_5$=an additional bond, and $R_6$, $R_7$ are alkyl and $R_8$ is H or alkyl, and N-oxides, esters and salts thereof, processes for their production and their uses as pharmaceuticals e.g. as $K^+$-channel openers, bronchodilators and asthma prophylactic agents.

20 Claims, No Drawings

2,2-DIALKYL- AND 2,2-DIALKYL-3,4-DIHYDRO-3-HYDROXY-2H-1-BENZOPYRANS

This is a continuation of application Ser. No. 08/256,803, filed Jul. 22, 1994 now abandoned, which is a 371 of International Application No. PCT/EP92/02719, filed on Nov. 25, 1992.

The present invention relates to novel 2,2-dialkyl- and 2,2-dialkyl-3,4-dihydro-3-hydroxy-2H-1-benzopyrans and salts, esters and N-oxides thereof and to processes for their production, as well as to their use as pharmaceuticals and pharmaceutical compositions comprising them.

More particularly the present invention provides in its broadest aspect:

1. A 2,2-di($C_{1-5}$alkyl)-, or trans-2,2-di($C_{1-5}$alkyl)-3,4-dihydro-3-hydroxy-,-6-(pyridin-4-yl)-2H-1-benzopyran having a carboxamido moiety at the 4-position and wherein the pyridin-4-yl group is substituted at the 2- and/or 3-position by one or two members selected from the group comprising $C_{1-5}$alkyl, $C_{1-5}$hydroxyalkyl and $C_{1-5}$ (alkoxyalkyl), or N-oxide thereof; or a physiologically-hydrolyzable and -acceptable ester of such a benzopyran or N-oxide or an acid addition or quarternary ammonium salt of such a benzopyran, N-oxide or ester.

Alkyl groups and moieties of compounds as defined under 1. above may be branched or straight chain. Preferred significances for substituents at the 2-position of the benzopyran nucleus as well as at the 2 and/or 3 position of the pyridinyl group are as set forth below in relation to formula I for $R_6$ and $R_7$, and $R_1$ and $R_2$.

As hereinafter described, compounds of the present invention, e.g. as defined under 1 above, have potassium ($K^+$) channel opening activity [see e.g. Cook et al., "Potassium Channels: Structure, Classification, Function and Therapeutic Potential", ed. N. S. Cook, Ellis Horwood, Chichester (1990), p.p. 181–255]. Benzopyran derivatives which are carboxamido-substituted at the 4-position, having $K^+$-channel opening activity are extensively described in the art and comprise a substantial and recognizable compound class. The 4-carboxamido moiety in the compounds of the invention may comprise any of those known and described in the art in relation to $K^+$-channel opening benzopyrans, including N-substituted, for example cyclic, carboxamido moieties. Preferred carboxamido moieties in relation to the compounds of the invention are those of the formula —N($R_9$)-$COR_{10}$ as defined below.

As will be appreciated, the benzopyran nucleus of compounds defined under 1 may bear substituents in addition to those specifically defined. In particular they may, for example, be 7-$C_{1-5}$alkyl substituted, especially 7-methyl substituted, e.g. as hereinafter indicated in relation to formula I.

In accordance with the present invention 2,2-di-($C_{1-5}$alkyl)-3,4-dihydro-3-hydroxy-6-(pyridin-4-yl)-2H-1-benzopyrans and/or -oxides, esters, and salts thereof as defined under 1 above are preferred. The 3-hydroxy group and the 4-carboxamido moiety in such compounds are disposed in the trans-configuration as specified under 1. For this compound group (3S, 4R)-enantiomers will generally be preferred, whether in pure or substantially pure form or in isomeric, e.g. racemic, mixture as hereinafter described in relation to compounds of formula I.

In a more specific aspect the present invention provides:

2. A compound of formula I

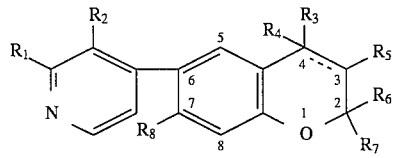

wherein $R_1$ and $R_2$ are independently, hydrogen, $C_{1-5}$alkyl, $C_{1-5}$hydroxyalkyl or $C_{1-5}$ (alkoxyalkyl), whereby at least one of $R_1$ and $R_2$ is other than hydrogen, $R_3$ is a group of formula —N($R_9$)—$COR_{10}$ wherein $R_9$ is hydrogen and $R_{10}$ is pyridyl or $R_9$ and $R_{10}$ together are 1,3-butadienylene or represent a group of formula

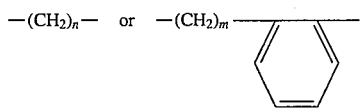

in which n is an integer of from 3 to 5 inclusive and m is 1 or 2, $R_4$ is hydrogen and $R_5$ is hydroxy in the trans position with respect to $R_3$, or $R_4$ and $R_5$ together represent an additional bond as indicated by the dotted line, $R_6$ and $R_7$ are, independently, $C_{1-5}$alkyl, and $R_8$ is hydrogen or $C_{1-5}$alkyl, or N-oxide thereof; or a physiologically-hydrolyzable and -acceptable ester of such a compound or N-oxide, or an acid addition or quarternary ammonium salt of such a compound, N-oxide or ester.

Alkyl groups as $R_1$, $R_2$, $R_6$, $R_7$ and $R_8$, as well as alkyl moieties of hydroxyalkyl and alkoxyalkyl groups as $R_1$ and $R_2$ may be branched or straight chain. Alkoxyalkyl groups are preferably ($C_{1-4}$alkoxy)-methyl, in particular methoxymethyl.

Preferred hydroxyalkyl groups are hydroxymethyl. $R_6$ and $R_7$ are both preferably methyl. $R_8$ is preferably hydrogen or methyl, most preferably hydrogen.

In a preferred group of compounds of formula I, $R_1$ has any of the meanings given above in relation to formula I and $R_2$ is hydrogen or $C_{1-5}$alkyl (especially methyl), preferably hydrogen.

In a further preferred group of compounds of formula I, in the definition of $R_3$, $R_9$ is hydrogen and $R_{10}$ is pyridyl (especially 3-pyridyl) or $R_9$ and $R_{10}$ together are 1,3-butadienylene, trimethylene or tetramethylene. Most preferably $R_9$ and $R_1$ together are tetramethylene.

Preferably $R_4$ is hydrogen and $R_5$ is hydroxy. Benzopyrans of the invention, for example Compounds of formula I, form N-oxides, e.g. at the nitrogen atom of the 6-pyridinyl group. Such N-oxides have comparable activity (as hereinafter described) and tolerability to the parent compounds and also form part of the present invention.

By "physiologically-hydrolyzable and -acceptable ester" as used herein is meant an ester in which a hydroxy group (e.g., in relation to formula I, hydroxy groups $R_5$ and/or the hydroxy moiety of any hydroxyalkyl group present as $R_1$ and/or $R_2$) is esterified and which is hydrolyzable under physiological conditions to yield an acid which is itself physiologically tolerable at doses to be administered. As will be appreciated such esters are pro-drug forms of conventional type and have comparable activity and tolerability to the parent compounds. Examples of such esters include, e.g. acetates.

Acid addition salts, e.g. of compounds of formula I, their N-oxides and defined esters thereof, include salts with both inorganic and organic acids. Such salts also have comparable activity to the free compounds, N-oxides and esters. Pharmaceutically acceptable acid addition salts for pharmaceutical use in accordance with the present invention as hereinafter described include e.g. hydrochloric, sulfuric and fumaric acid salts.

Quarternary ammonium salts, e.g. of compounds of formula I, their N-oxides and defined esters thereof, include e.g. salts with organo-halides, e.g. alkyl halides. Pharmaceutically acceptable quarternary ammonium salts for pharmaceutical use in accordance with the present invention include e.g. such salts with methyl iodide.

For pharmaceutical use in accordance with the present invention ester forms as aforesaid are generally less preferred.

Compounds of formula I in which $R_4$ is hydrogen and $R_5$ is hydroxy, as well as their N-oxides, esters and salts as aforesaid, have the configuration (3S*,4R*), i.e. the configuration of the groups $R_3$ and $R_5$ at the 3- and 4-positions is trans. Compounds of the invention thus exist in enantiomeric form, i.e. as optically active antipodes having the [3S, 4R] or [3R, 4S] configuration. The present invention is to be understood as embracing both the individual enantiomers (optically active, [3S, 4R] or [3R, 4S], antipodes) as well as mixtures, e.g. racemic mixtures, thereof.

In that pharmaceutical utility in accordance with the invention is believed to reside, or reside predominantly, in the [3S, 4R] enantiomers, these are preferred. Suitably the said [3S, 4R] enantiomers will be, or will be employed in accordance with the invention, in purified form, i.e. comprising less than 50% enantiomeric contaminants, more suitably in pure or substantially pure form, e.g. comprising less than 10%, preferably 5% or less, e.g. 1 or 2% or less of [3R, 4S] enantiomeric contaminants.

In addition to the foregoing the present invention also provides:

3. A process for the production of a benzopyran as defined under 1 above, for example a compound of formula I as defined under 2 above, or N-oxide thereof, or physiologically-hydrolyzable and -acceptable ester of such a benzopyran or N-oxide or acid addition or quarternary ammonium salt of such a benzopyran, N-oxide or ester, which process comprises:

i) for the production of a benzopyran as aforesaid:

i$^1$) reacting a 1a,7b-dihydro-2,2-di($C_{1-5}$alkyl)-6-(pyridin-4-yl)-2H-oxireno[c][1]benzopyran wherein the pyridin-4-yl group is substituted at the 2- and/or 3-position by one or two members selected from the group comprising $C_{1-5}$alkyl, $C_{1-5}$-hydroxyalkyl and $C_{1-5}$-(alkoxyalkyl), for example a compound of formula II

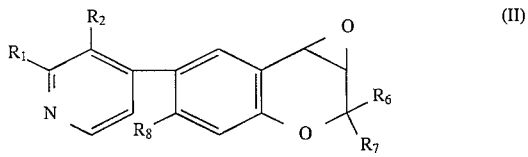

wherein $R_1$, $R_2$, $R_6$, $R_7$ and $R_8$ have the meanings for formula I above, with an alkali metal salt of a carboxamide, for example a compound of formula III

wherein $R_9$ and $R_{10}$ have the meanings given for formula I above and $M^+$ is a lithium, sodium or potassium ion; or i$^2$) acylating and, when required, alkylating the amino group of a 2,2-di($C_{1-5}$alkyl)- or trans-2,2-di($C_{1-5}$alkyl)-3,4-dihydro-3-hydroxy-4-amino-6-(pyridin-4-yl)-2H-1-benzopyran wherein the pyridin-4-yl group is substituted at the 2- and/or 3-position by one or two members selected from the group comprising $C_{1-5}$alkyl, $C_{1-5}$hydroxyalkyl and $C_{1-5}$(alkoxyalkyl), for example, reacting a compound of formula IV

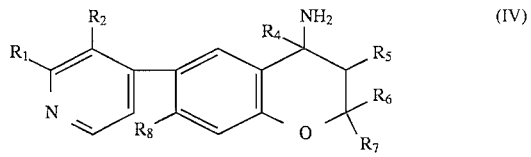

wherein $R_1$, $R_2$ and $R_4$ to $R_8$ have the meanings given for formula I, with a compound of formula V, V' or V''

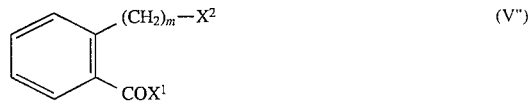

wherein $R'_{10}$ is pyridyl and $X^1$ and $X^2$ are leaving groups;

ii) for the production of a benzopyran N-oxide or physiologically-hydrolyzable and -acceptable ester of a benzopyran or benzopyran N-oxide as aforesaid, esterifying a benzopyran or benzopyran N-oxide as defined under 1 above having a free hydroxy group or moiety to introduce an appropriate ester grouping, for example reacting a compound of formula I as hereinbefore defined wherein $R_5$ is hydroxy and/or at least one of $R_1$ and $R_2$ is $C_{1-5}$ hydroxyalkyl or N-oxide thereof with an appropriate acid halide or anhydride, and/or oxidizing a benzopyran or physiologically-hydrolyzable and -acceptable ester thereof as defined under 1 above, for example oxidizing a compound of formula I as hereinbefore defined or physiologically-hydrolyzable and -acceptable ester thereof; and recovering the obtained benzopyran, benzopyran N-oxide or physiologically-hydrolyzable and-acceptable ester thereof in free or in acid addition or quarternary ammonium salt form.

Process step i$^1$) above may be carried out in accordance with methods known in the art, for example by reaction at ambient temperatures to reflux in the presence of an inert solvent or diluent such as tetrahydrofuran or dimethylsulfoxide. Suitably the required alkali metal salt, e.g. compound of formula III, is pre-formed in situ, for example as described in Examples 1 to 11 and 21 hereinafter. By appropriate use of e.g. Na salts, both benzopyrans and dihydro-benzopyrans of the invention may be obtained, e.g. as illustrated in Examples 11 and 12 hereinafter. Use of lithium salts leads primarily or exclusively to the preferred dihydro-benzopyrans of the invention as illustrated in Examples 1 to 10 hereinafter.

Process step i$^2$) may also be carried out in accordance with methods known in the art. Suitable leaving groups $X^1$ are halogen and activated ester groups and suitable leaving groups $X^2$ are halogen. Reaction is suitably carried out at temperatures of from 0° to 100° C. in an inert solvent or diluent such as acetonitrile or dichloromethane, preferably in the presence of an acid binding agent, e.g. trialkylamine or alkali metal carbonate. The procedure is illustrated in Examples 13 to 20 hereinafter.

Process step ii) may be carried out in accordance with conventional acylation/N-oxidation procedures, e.g. for the obtention of N-oxides by treatment with hydrogen peroxide, m-chloroperbenzoic acid or Collin's reagent ($CrO_3 \cdot Py_2$) as hereinafter illustrated in Example 23.

Initially obtained free bases may be converted into acid addition or quarternary ammonium salts by reaction with acids or e.g. alkyl, for example methyl, halides, and vice versa.

Employing racemates of the formula II and formula IV compounds, 4-carboxamido-3,4-dihydro-3-hydroxy-benzopyrans obtained will be in the form of the trans-racemate [i.e. comprising the (3S, 4R) plus (3R, 4S) isomers]. Obtained racemates may be separated to provide the individual (3R, 4S) or (preferred) (3S, 4R) enantiomer, e.g. chromatographically using a chiral stationary phase. Where individual (3S, 4R) enantiomers are-desired, however, this is preferably achieved using the corresponding isomer as starting material, i.e. in relation to formula II, the 3S, 4S-antipode and, in relation to formula IV, the 3S, 4R-antipode. These are suitably produced as hereinafter described in relation to reaction sequence A.

As will be appreciated, variants of or alternatives to the above procedures may be employed as known in the art, e.g. for the interconversion of initially obtained compounds or for the introduction of alternative carboxamido groups at the 4-position. Labile groups may be protected e.g. during acylation procedures, employing conventional protecting, e.g. hydroxy-protecting groups. In addition, initially obtained benzopyrans may, if desired, be converted to corresponding benzopyrans by dehydration across the 3,4-linkage, again in accordance with standard techniques. Further alternatives will be apparent to those skilled in the art.

Compounds of the formula II may be prepared in accordance with the following general reaction sequence A Starting materials of formula IV may be prepared from the corresponding compounds of formula II by reaction with ammonia, e.g. in accordance with the general procedures hereinafter illustrated in Example 24.A.6'.

Proceeding via steps (iii) and (iv), the formula II compound is obtained as the cis-racemate, i.e. comprising the (3R, 4R) and (3S, 4S) antipodes. Step v involves introduction of an appropriate chiral acyl group [in sequence A, by way of example, (R)-α-methoxyphenylacetyl]. The chiral racemate VIII may readily be separated by column chromatography or fractional recrystallization into its individual (3R, 4S) and (3S, 4R) antipodes. By use of the (3R, 4S) antipode and proceeding via step (vi) compound II starting materials may be obtained in pure or substantially pure (3S, 4S) enantiomeric form.

Compounds of formula VI may be prepared in accordance with the following general reaction sequence B

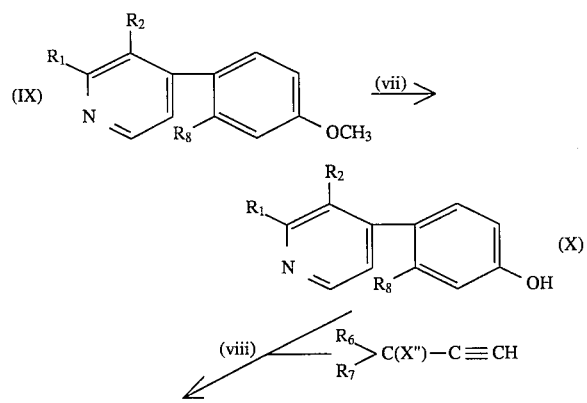

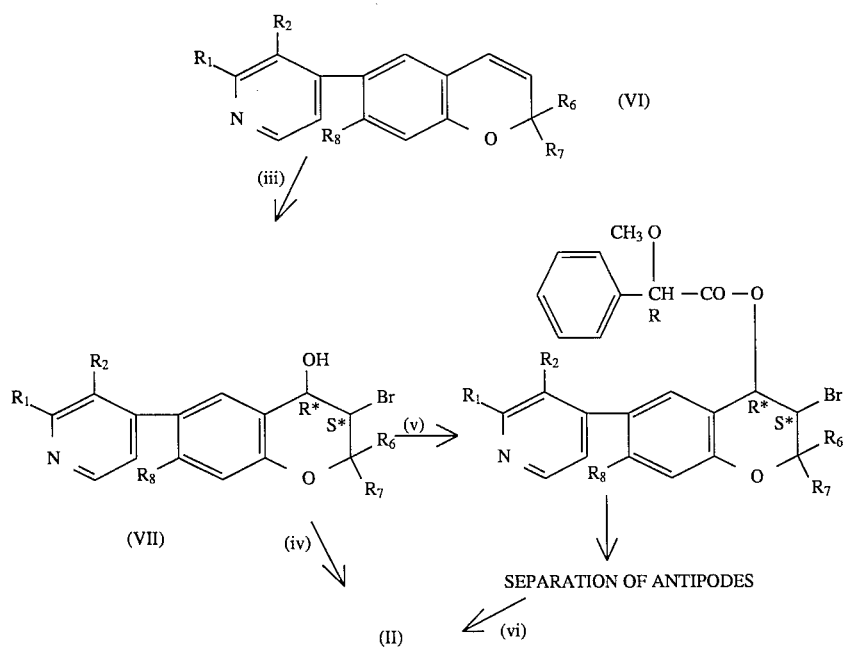

Process steps (iii) through (vi) may be carried out by conventional means, e.g. in accordance with the general procedures hereinafter illustrated in Examples 24.A.4, A.5, A.5'a, and A.5'b.

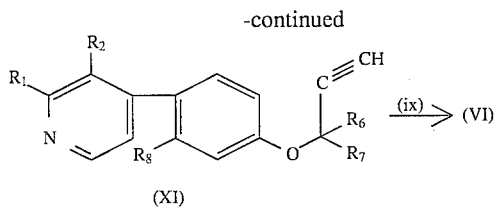

(XI)

in which X" is a leaving group, suitably a halogen atom, e.g. chlorine. Steps (vii) to (ix) may be carried out by conventional means, e.g. in accordance with the general procedures hereinafter illustrated in Examples 24.A.2 and A.3, steps (viii) and (ix) being carried out in Example 24.A.3 without purification of the intermediate. As in Example 24.A.2 step (vii) is suitably carried out in an aprotic solvent such as acetone, in the presence of a base such as $K_2CO_3$ and a catalyst such as KI.

Compounds of formula (IX) may be prepared by a variety of possible routes, for example as shown in the following general reaction sequence C 24.A.1a and b and 24.A.1a' and b' respectively. In general, procedure via steps (x) and (xi) will be preferred for larger scale synthesis.

When it is desired to produce compounds of the invention in which $R_1$ and/or $R_2$ are hydroxyalkyl or alkoxyalkyl, this can also be achieved by conversion of alkyl substituents as $R_1/R_2$. Similarly methyl substituents as $R_1/R_2$ can if desired, be converted to higher alkyl substituents. Conveniently such conversion reactions are carried out at the formula VI stage of synthesis employing conventional techniques, e.g. in accordance with the general procedures hereinafter illustrated in Examples 24.E.3, F.3, G.3.a+G.3.b and H.3.a+H.3.b.

Compounds of formula VI wherein $R_8$ is other than hydrogen may more conveniently be prepared in accordance with the following reaction sequence D.

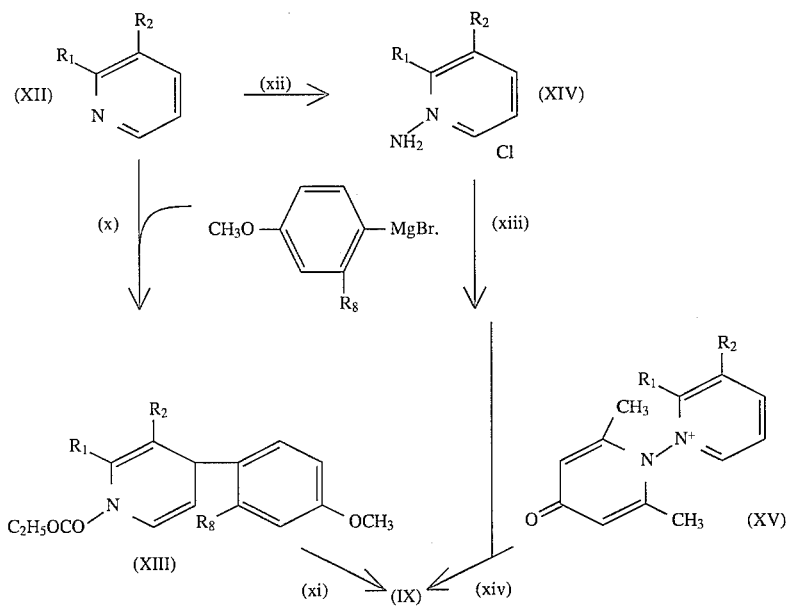

Process steps (x) and (xi), and (xii) through (xiv), may be carried out by conventional means, e.g. in accordance with the general procedures hereinafter illustrated in Examples

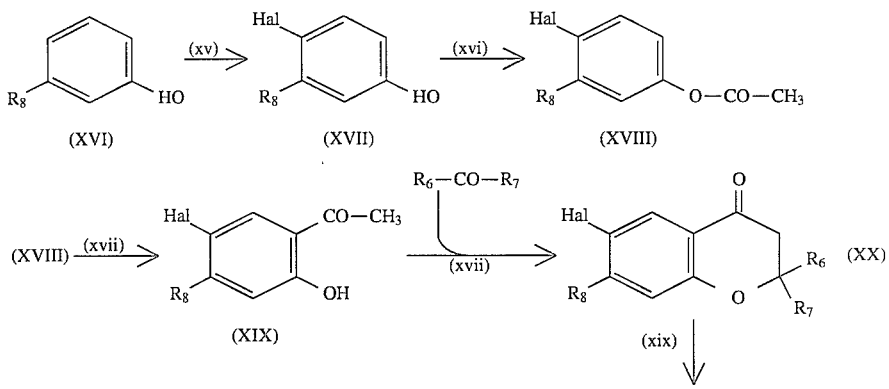

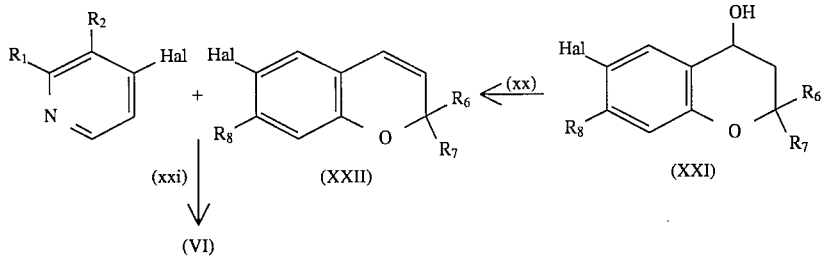

in which Hal is halogen, e.g. bromine, and Re is $C_{1-5}$alkyl. Process steps (xv) through (xxi) may be carried out by conventional means, e.g. in accordance with the procedures hereinafter illustrated in Example 24.I.

Intermediates illustrated above and in the accompanying Examples, notably intermediates of formulae II, IV and VI to VIII are new. Such intermediates, in particular the intermediates of formulae II and IV, and processes for their production also constitute part of the present invention.

The following Examples are illustrative of the processes of the present invention. All NMR spectra are recorded at 360 MHz. All temperatures are in degrees celsius and are uncorrected.

EXAMPLE 1

Production of (−)-(3S, 4R)-1-[3,4-dihydro-2,2-dimethyl-3-hydroxy-6-(2-methylpyridin-4-yl)-2H-1-benzopyran-4-yl]-2-piperidinone [FORMULA I: $R_1=R_6=R_7=CH_3$; $R_2=R_4=R_8=H$; $R_5=$—OH;

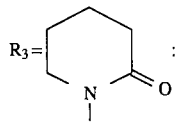

pure or substantially pure (3S, 4R) enantiomers].

A stirred solution of 2-piperidinone (19.8 g) in dry tetrahydrofuran (400 ml) at 10° C. under argon is treated with a solution of lithium bi (trimethylsilyl) amide (200 ml/1.0M) in tetrahydrofuran and stirred at room temperature for 2h. The resulting suspension is treated with a solution of (−)-(3S, 4S)-4-(1a, 7b-dihydro-2,2-dimethyl-2H-oxireno [c][1]-benzopyran-6-yl)-2-methylpyridine (26.7 g; see Example 24.A.5' hereinafter) in dry tetrahydrofuran (150 ml) and heated under reflux for 31 h. The mixture is cooled to 15° C., treated with a saturated aqueous solution of $NH_4Cl$ (300 ml) and extracted with ethyl acetate (2×150 ml). The combined extracts are washed with brine (300 ml), dried ($Na_2SO_4$) and filtered. The solvent is evaporated off under reduced pressure to give a crude product which is purified by chromatography (silica gel, 5% $C_2H_5OH$ in $CH_2Cl_2$) and recrystallized from $C_2H_5OH$ -pentane to give the title compound, m.p.=192° C., $[\alpha]_D^{20}=-83.2°$ (c=1.06, $C_2H_5OH$). M.P. for the hemimaleate salt= 146°–148° C.

The following compounds of formula Ia

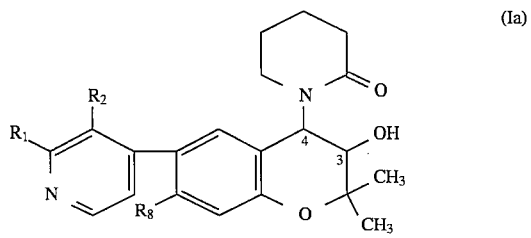

are prepared analogously, production of the required oxireno starting material being illustrated in the Example indicated in the right-hand column of the table.

All compounds listed in the table are in the form of the trans racemate.

| EXAMPLE | $R_1$ | $R_2$ | $R_8$ | m.p. °C. | STARTING MATERIAL ACCORDING TO EXAMPLE 24 |
|---|---|---|---|---|---|
| 2 | $CH_3$— | H | H | 184–185 | A.5. |
| 3 | H | $CH_3$— | H | 205–206 | D.5. |
| 4 | $C_2H_5$— | H | H | 196–197 | B.5. |
| 5 | HO—$CH_2$— | H | H | 200–201 | G.5. |
| 6 | $CH_3O$—$CH_2$— | H | H | 182–183 | H.5. |
| 7 | $nC_3H_7$— | H | H | 178–179 | E.5. |
| 8 | $iC_4H_9$— | H | H | 210–211 | F.5. |
| 9 | $CH_3$— | $CH_3$— | H | 201–202 | C.5. |
| 10 | $CH_3$— | H | $CH_3$— | 219–221 | I.5. |

EXAMPLE 11

Production of 1-[2,2-Dimethyl-6-(2-methylpyridin-4-yl)-2H-1-benzopyran-4-yl]-2-piperidinone [Formula I: $R_1=R_6=R_7=CH_3$—; $R_2=R_8=H$; $R_4+R_5=$additional bond;

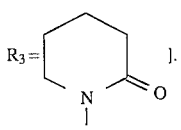

A stirred solution of 2-piperidinone (0.90 g in dry dimethylsulphoxide (20 ml) is treated with NaH (0.48 g of a 55% dispersion in oil) and stirred at 50° C. for 30 min. under argon. The mixture is cooled to 10° C and treated with a solution of (±)-4-(1a, 7b-dihydro-2,2-dimethyl-2H-oxireno-[c][1]benzopyran-6-yl)-2-methylpyridine (2.67 g, see Example 24.A.5) and stirred for 14 h at room temperature under argon. The solvent is evaporated off under reduced pressure and the residue treated with saturated aqueous NH$_4$Cl (200 ml) and extracted with CH$_2$Cl$_2$ (3×100 ml). The combined extracts are dried (Na$_2$SO$_4$), filtered and the solvent is evaporated off under reduced pressure to yield a mixture. This is separated by chromatography (silica gel, 2% C$_2$H$_5$OH in CH$_2$Cl$_2$) to yield a less polar product (A) which is recrystallized from ethyl ether-pentane to give the title compound and a more polar compound (B) which is recrystallized from CH$_2$Cl$_2$-diethyl ether to give the same product as that of Example 2 above. M.P. for the title compound= 95°–98° C.

EXAMPLE 12

Production of 1-[2,2-dimethyl-6-(3-methylpyridin-4-yl)-2H-1-benzopyran-4-yl]-2-piperidinone [Formula I: R$_2$=R$_6$=R$_7$=CH$_3$—; R$_1$=R$_8$=H; R$_4$+R$_5$=additional bond;

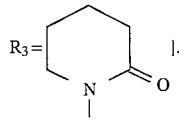

The title compound is obtained together with the product of Example 3 above, starting from the product of Example 24.D.5. hereinafter and proceeding analogously to Example 11 above. Physical characteristics for the title compound: $^1$H-NMR (δ-d$^6$ DMSO): 1.41 (s,3H), 1.45 (s,3H), 1.77–1.96 (m,3H), 2.26 (s,3H), 2.27–2.68 (m,3H), 3.37–3.58 (m,2H), 5.83 (s,1H), 6.92 (d,1H), 7.14–7.20 (m,2H), 7.36 (m,1H), 8.39 (d,1H) and 8.45 (s,1H).

EXAMPLE 13

Production of (+)-(3S, 4R)-[3,4-dihydro-2,2-dimethyl-3-hydroxy-6-(2-methylpyridin-4-yl)-2H-1-benzopyran]-3-pyridine-carboxamide [Formula I: R$_1$=R$_6$=R$_7$=CH$_3$; R$_2$=R$_4$=R$_8$=H;

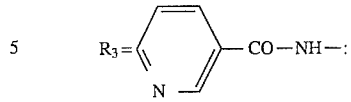

pure or substantially pure (3S, 4R) enantiomer]

A stirred solution of (+)-(3S, 4R)-4-amino-3,4-dihydro-2,2-dimethyl-6-(2-methylpyridin-4-yl)-2H-1-benzopyran-3-ol (0.65 g: see Example 24.A.6' hereinafter), triethylamine (0.50 g) and 4-dimethylaminopyridine (0.002 g) in dry CH$_2$Cl$_2$ (30 ml) at 2° C. under argon is treated with nicotinoyl chloride, hydrochloride (0.445 g). The mixture is stirred for 2 hours at room temperature after which the mixture is treated with aqueous Na$_2$CO$_3$ (100 ml/2M) and extracted with 3:1 CH$_2$Cl$_2$/CH$_3$OH (3×100 ml). The combined extracts are washed with brine, dried (Na$_2$SO$_4$), filtered and the solvent evaporated off under reduced pressure to yield an oil. The oil is purified by chromatography (silica gel, 2% C$_2$H$_5$OH in CH$_2$Cl$_2$) and recrystallized from C$_2$H$_5$OH-diethyl ether to give the title compound in enantiomerically pure or substantially pure form, m.p. 247°–248° C., [α]$_D^{20}$=+19.8 (c=0.965, C$_2$H$_5$OH).

The following compounds of formula Ib

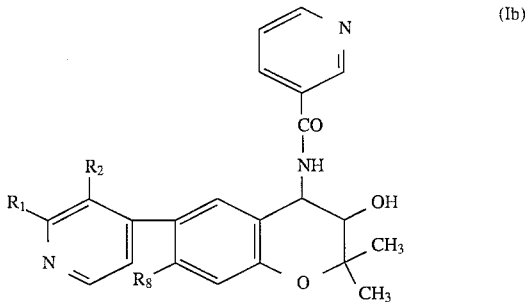

are prepared analogously, production of the required 4-amino-benzopyran-3-ol starting material being illustrated in the example indicated in the right hand column of the table.

All compounds listed in this table are in the form of the trans racemate.

| EXAMPLE | R$_1$ | R$_2$ | R$_8$ | m.p. °C. | STARTING MATERIAL ACCORDING TO EXAMPLE 24 |
| --- | --- | --- | --- | --- | --- |
| 14 | CH$_3$— | H | H | 230–231 | A.6. |
| 15 | C$_2$H$_5$— | H | H | 192–193 | B.6. |
| 16 | CH$_3$OCH$_2$— | H | H | 206–208 | H.6. |
| 17 | nC$_3$H$_7$— | H | H | 206–207 | E.6. |
| 18 | iC$_4$H$_9$— | H | H | 240–241 | F.6. |
| 19 | CH$_3$— | CH$_3$— | H | 239–241 | C.6 |
| 20 | CH$_3$— | H | CH$_3$— | 234–236 | I.6 |

EXAMPLE 21

Production of trans-(±)-1-[3,4-dihydro-2,2-dimethyl-3-hydroxy-6-(2-methylpyridin-4-yl)-2H-1-benzopyran-4-yl]-2 (1H)-pyridinone [Formula I: R$_1$=R$_6$=R$_7$=CH$_3$—; R$_2$=R$_4$=R$_8$=H;

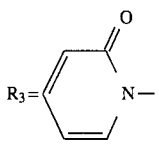

as the trans racemate]

A stirred solution of 2-hydroxypyridine (0.42 g) in dry $C_2H_5OH$ (20 ml) is treated with NaH(0.21 g of a 55% dispersion in oil) and stirred at room temperature for 15 min. under argon. The mixture is then cooled to 2° C. and treated with a solution of (±)-4-(1a, 7b-dihydro-2,2-dimethyl-2H-oxireno [c][1]benzopyran-6-yl)-2-methylpyridine (1.07 g (see Example 24.A.5) and stirred for 96 h at room temperature. The solvent is evaporated off under reduced pressure and the residue treated with saturated aqueous $NH_4Cl$ (100 ml) and extracted with $CH_2Cl_2$ (3×100 ml). The combined extracts are dried ($Na_2SO_4$), filtered and the solvent is evaporated off under reduced pressure to yield the crude product which is purified by chromatography (silica gel, 2% $C_2H_5OH$ in $CH_2Cl_2$) and recrystallized from $C_2H_5OH$-diethyl ether to give the title compound, m.p. 213°–214° C.

EXAMPLE 22

Production of trans-(±)-2-[3,4-Dihydro-2,2-dimethyl-3-hydroxy-6-(2-methyl-pyridin-4-yl)-2H-1-benzopyran-4-yl]-2,3-di hydro-1H-isoindol-1-one [Formula I: $R_1=R_6=R_7=CH_3$—; $R_5=$—OH $R_2=R_4=R_8=H$;

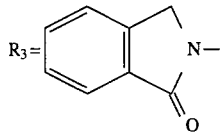

as the trans racemate]

A stirred solution of trans-(±)-4-amino-3,4-dihydro-2,2-dimethyl-6-(2-methylpyridin-4-yl)-2H-1-benzopyran-3-ol (2.84 g) (see Example 24.A.6) and 2-bromomethylbenzoic acid methyl ester (2.30 g) in dry acetonitrile (100 ml) is treated with KI (0.84 g) and then $K_2CO_3$ (4.20 g) under argon. The reaction mixture is stirred for 1 h at 20° C., 1 h at 60° C. and then 15 h at 85°. The solvent is evaporated off under reduced pressure and the residue treated with $H_2O$ (300 ml) and extracted with 2% $CH_3OH$ in $CH_2Cl_2$ (4×150 ml). The combined extracts are washed with sodium thiosulphate solution (100 ml/2%), dried ($Na_2SO_4$) and filtered. The solvent is evaporated off under reduced pressure to yield a crude product which is purified by chromatography (silica gel, 5% $C_2H_5OH$ in $CH_2Cl_2$) and recrystallized from $C_2H_5OH$-acetone to give the title compound, m.p. 222°–224° C.

EXAMPLE 23

Production of (−)-(3S, 4R)-4-[3,4-Dihydro-2,2-dimethyl-3-hydroxy-4-(2-oxo-piperidin-1-yl)-2H-1-benzopyran-6-yl]-2-methylpyridine-N-oxide A solution of the product of Example 1 (2.6 g) in $CH_2Cl_2$ (40 ml) is treated with 3-chloroperoxybenzoic acid (1.92 g of 90%) and stirred at room temperature for 18 h. The solvent is evaporated off under reduced pressure to yield the crude product which is purified by chromatography (silica gel, 5% $C_2H_5OH$ in $CH_2Cl_2$) and recrystallized from acetone-diethyl ether to give the title compound, m.p. 202°–205° C.

EXAMPLE 24

Production of starting materials for Examples 1 through 23
A.1. Preparation of 4-(4-methoxyphenyl)-2-methylpyridine
A.1.a. 4-(4-Methoxyphenyl)-2-methyl-1(4H)-pyridinecarboxylic acid ethyl ester Ethyl chloroformate (10.85 g) is added to a stirred mixture of 2-picoline (9.30 g) and copper (I) iodide (0.77 g) in dry tetrahydrofuran (150 ml), at −20° C. under argon. The whole is stirred for 3 hours at −20° C. and then treated dropwise with a solution of 4-methoxyphenyl magnesium bromide, prepared from 4-bromoanisole (18.7 g) and Mg turnings (2.64 g) in dry tetrahydrofuran (100 ml) at such a rate that the temperature remains between −15° and −20° C. The mixture is stirred at −15° for 1 hour, and 16 hours at 20° C. and then treated with a saturated aqueous solution of $NH_4Cl$ (300 ml) and extracted with ethyl acetate (4×200 ml). The combined extracts are dried ($Na_2SO_4$), filtered and the solvent is evaporated off under reduced pressure to yield the crude product. This is purified by chromatography (silica gel, 50% toluene in hexane) to give the title compound as a pale yellow oil.

A.1.b 4-(4-Methoxyphenyl)-2-methylpyridine

The product of step A.1.a (16.9 g) and sulphur (2.0 g) in decahydronaphthalene (100 ml) is stirred at 200° C. for 3 hours. The solvent is evaporated off under reduced pressure and the residue dissolved in ethyl acetate (500 ml) and extracted with HCl (3×200 ml of 2M). The combined extracts were washed with ethyl acetate (2×100 ml), basified with ice-cooling to pH 11 with NaOH and extracted with $CH_2Cl_2$ (3×200 ml). The combined extracts are dried ($Na_2SO_4$), filtered and the solvent evaporated off under reduced pressure to yield the crude product. This is purified by chromatography (silica gel, 2% $C_2H_5OH/CH_2Cl_2$) and recrystallized from $C_2H_5OH$-ethyl acetate to yield the title compound, m.p. 88°–91° C.

The title compound may alternatively be produced via the following route:

A.1a' 2,2',6'-Trimethyl-4-oxo-1,1' (4'H)-bipyridinium-tetrafluoroborate

2-Methylpyridine (111.7 g) is added to a freshly prepared solution of hydroxylamine-O-sulphonic acid (45.2 g, 90%) in $H_2O$ (260 ml) at 0° C. The mixture is heated to 95° C., stirred for a further 45 min, cooled to 10° C. and cautiously treated with $K_2CO_3$ (55 g). The mixture is washed with diethyl ether (2×100 ml) and the water evaporated off at 40° C. under reduced pressure. The residue is treated with $C_2H_5OH$ (600 ml) and the $K_2SO_4$ precipitate removed by filtration. The filtrate is treated with HCl (120 ml of 18M) and evaporated to dryness at 50° C. under reduced pressure to give a residue which is treated with dehydroacetic acid (68.6 g) and HCl (150 ml of 18M) and heated under reflux for 90 min. The solution is evaporated to dryness at 50° under reduced pressure and the residue stirred for 15 min with $C_2H_5OH$ (200 ml), filtered and the precipitate washed with $C_2H_5OH$ (200 ml). The combined filtrate and washings are treated with tetrafluoroboric acid in ethyl ether (50 ml of 50%) and diluted with diethyl ether (250 ml). On standing the title compound crystallises out and is filtered off and dried in vacuo at 20° C., m.p. 206°–208° C.

A.1.b' 4-(4-Methoxyphenyl)-2-methyl-pyridine

A stirred solution of 4-methoxyphenylmagnesium bromide prepared from 4-bromoanisole (56.1 g) and Mg turnings (7.92 g) in dry tetrahydrofuran (400 ml) at 0°–5° is treated with the product of step (A.1.a') (30.2 g) under an argon atmosphere. The mixture is stirred at room temperature for 48 h, washed with saturated aqueous $NH_4Cl$ (300 ml) and the aqueous phase is extracted with $CH_2Cl_2$ (3×100 ml). The combined tetrahydrofuran solution and $CH_2Cl_2$ extracts are dried ($Na_2SO_4$), filtered and the solvent is evaporated off under reduced pressure to yield crude 4'-(4-methoxyphenyl)-2,2',6'-trimethyl-[1,1' (4H, 4'H)-bipyridin] -4-one. The crude product is dissolved in dry dimethylformamide (400 ml) and heated under reflux for 4 h. The solvent is evaporated off under reduced pressure to give a residue which is purified by chromatography (silica gel, 2% $C_2H_5OH$ in $CH_2Cl_2$) and recrystallized from $C_2H_5OH$ to yield the title compound m.p. 88°–91°.

A.2. Preparation of 4-(4-hydroxyphenyl)-2-methylpyridine

A solution of the product of Example A.1. (6.45 g) in HBr (100 ml of 48%) is heated at 135° for 3 h. The excess HBr is evaporated off under reduced pressure to give a residue which is neutralized with aqueous $NaHCO_3$ and extracted with 3:1 $CH_2Cl_2/C_2H_5OH$ (3×150 ml). The combined extracts are dried ($Na_2SO_4$), filtered and the solvent is evaporated off under reduced pressure to give the crude product. This is recrystallized from $C_2H_5OH$-diethyl ether to give the title compound, m.p. 203°–204°.

A.3. preparation of 2,2-dimethyl-6-(2-methylpyridin-4-yl)-2H-1-benzopyran.

A stirred mixture of the product of Example A.2. (4.07 g), anhydrous $K_2CO_3$ (6.9 g) and KI (1.0 g) in dry acetone (75 ml) under argon is treated with 3-chloro-3-methylbutyne (5.65 g) and heated under reflux for 120 h. The mixture is filtered and the solvent evaporated off under reduced pressure to yield crude 4-[4-(1,1-dimethyl-2-propynyl)oxyphenyl]-2-methylpyridine. This is dissolved in 1,2-dichlorobenzene (50 ml) and heated at 170° for 1 h. The solvent is evaporated off under reduced pressure to give the crude title compound which is purified by chromatography (silica gel, 2% $C_2H_5OH$ in $CH_2Cl_2$), to give the title compound, m.p. 37°–40° C.

The following compounds may be prepared analogously to Example A.1 to A.3 above proceeding either via steps (A.1.a)+(A.1.b) or (A.1.a'+(A.1.b'); all are recovered as oils:

B.3. 2,2-Dimethyl-6-(2-ethylpyridin-4-yl)-2H-1-benzopyran;

C.3. 2,2-Dimethyl-6-(2,3-dimethylpyridin-4-yl)-2H-1-benzopyran;

D.3. 2,2-Dimethyl-6-(3-methylpyridin-4-yl)-2H-1-benzopyran.

E.3. Preparation of 2,2-Dimethyl-6-(2-propylpyridin-4-yl)-2H-1-benzopyran

To a stirred solution of the product of Example A.3. (5.02 g) in dry tetrahydrofuran (50 ml) at −25° C. under argon is added a solution of n-butyl lithium (12.5 ml, 1.6M) in hexane. The resulting mixture is stirred at 10° C. for 40 min, cooled to −5° C. and treated with ethyl iodide (2.4 ml). The mixture is allowed to warm to room temperature, stirred for an additional 2 h and then treated with saturated aqueous $NH_4Cl$ (100 ml) and extracted with ethyl acetate (2×100 ml). The combined extracts are dried ($Na_2SO_4$), filtered and the solvent is evaporated off under reduced pressure to yield the crude product which is purified by chromatography (silica gel, 10% acetone in hexane) to yield the title compound as an oil.

F.3. Preparation of 2,2-dimethyl-6-(2-i.butylpyridin-4-yl)-2H-1-benzopyran

The title compound, prepared analogously to Example E.3. employing isopropyl iodide in lieu of ethyl iodide, is obtained as an oil.

G.3. Preparation of 2,2-dimethyl-6-(2-hydroxymethylpyridin-4-yl)-2H-1-benzopyran acetate G.3.a 4-(2,2-Dimethyl-2H-1-benzopyran-6-yl)-2-methylpyridine-N-oxide A solution of the product of Example A.3. (13.4 g) in $CH_2Cl_2$ (200 ml) is treated with 3-chloroperoxybenzoic acid (13.5 g of 70%) and stirred at room temperature for 1 h. The solvent is evaporated off under reduced pressure to give a residue which is purified by chromatography (silica gel, 5% $C_2H_5OH$ in $CH_2Cl_2$) to give the title compound as a yellow gum.

G.3.b (2,2-Dimethyl-6-(2-hydroxymethylpyridin-4-yl)-2H-1-benzopyran acetate

A mixture of the product of step G.3.a (4.8 g) and acetic anhydride (50 ml) is heated at 80° C. under argon for 1 h. The solvent is evaporated off under reduced pressure to yield the crude product which is purified by chromatography (silica gel, 10% ethyl acetate in toluene) to give the title compound as an oil.

H.3. Preparation of 2,2-Dimethyl-6-(2-methoxymethylpyridin-4-yl)-2H-1-benzopyran H.3.a (2,2-Dimethyl-2H-1-benzopyran-6-yl)-2-pyridinemethanol A mixture of the product of Example G.3. (69.5 g), $Na_2CO_3$ (95.4 g), $H_2O$ (160 ml) and $C_2H_5OH$ (600 ml) is stirred at room temperature for 22 h. The mixture is filtered and the filtrate evaporated to dryness under reduced pressure to give a residue which is treated with $H_2O$ (400 ml) and extracted with $CH_2Cl_2$ (3×150 ml). The combined extracts are dried ($Na_2SO_4$) and the solvent is evaporated under reduced pressure to yield the crude product. This is purified by chromatography (silica gel, ethyl acetate) and recrystallized from pentane to give the title compound, m.p. 86°–88° C.

H.3.b (2,2-Dimethyl-2H-1-benzopyran-6-yl)-2-methoxymethyl pyridine

A stirred solution of the product of step H.3.a (8.0 g) in dry tetrahydrofuran (150 ml) at 15° C. under argon is treated with NaH (0.90 g of an 80% dispersion in oil) and stirred at room temperature for 45 min. Methyl iodide (4.26 g) is added and the mixture is stirred at room temperature for 18 h. The mixture is treated with saturated aqueous $NH_4Cl$ (200 ml) and extracted with ethyl acetate (2×200 ml). The combined extracts are dried ($Na_2SO_4$), filtered and the solvent is evaporated off under reduced pressure to yield the crude product. This is purified by chromatography (silica gel, 20% acetone in hexane) to give the title compound as an oil.

I. Preparation of 6-(2-methylpyridin-4-yl)-2,2,7-trimethyl-2H-1-benzopyran a. 4-Bromo-3-methylphenol acetate A stirred mixture of 4-bromo-3-methylphenol (184.1 g) and aqueous NaOH (850 ml, 2M) at 20° C. is treated with acetic anhydride (136 ml) and stirred at room temperature for 1 h. The suspension is extracted with diethyl ether (3×300 ml) and the combined extracts are washed with aqueous NaOH (2×100 ml 2M), dried ($Na_2SO_4$) and filtered. The solvent is evaporated off under reduced pressure to yield the title compound as an oil.

b. 1-(3-Bromo-2-hydroxy-5-methylphenyl)ethanone

A mixture of the product of step a (195.6 g) and aluminium chloride (152.6 g) is stirred under argon at 165° C. for 45 min. The cooled mixture is treated with ice-cold HCl (2000 ml, 2M) and extracted with $CH_2Cl_2$ (4×600 ml). The combined extracts are washed with brine, dried ($Na_2SO_4$), filtered and the solvent is evaporated off under reduced pressure to yield the crude product. This is purified by chromatography (silica gel, 10% toluene in hexane) and recrystallized from diethyl ether-hexane to give the title compound, m.p. 81°–82° C.

c. 6-Bromo-3,4-dihydro-2,2,7-trimethyl-2H-1-benzopyran-4-one

A mixture of the product of step b (48 g), acetone (31 ml) and pyrrolidine (21 ml) in dry benzene (500 ml) is stirred at room temperature for 3 h and then at reflux for 6 h with water formed being removed via a Dean-Stark apparatus. The cooled mixture is treated with HCl (200 ml, 2M), stirred for 10 min, basified with aqueous NaOH (1M) and extracted with $CH_2Cl_2$ (3×300 ml). The combined extracts are dried ($K_2CO_3$), filtered and the solvent is evaporated off under reduced pressure to yield the crude product. This is purified by chromatography (silica gel, 50% toluene in hexane) and recrystallized from diethyl ether-pentane to give the title compound, m.p. 95°–96° C.

d. 6-Bromo-3,4-dihydro-4-hydroxyl-2,2,7-trimethyl-2H-1-benzopyran

A stirred solution of the product of step c (26.9 g) in $C_2H_5OH$ (200 ml) at 5° C. is treated with sodium borohydride (1.95 g) and stirred at room temperature for 12 h. The solvent is evaporated off under reduced pressure to give a residue which is treated with $H_2O$ (500 ml) and extracted with diethyl ether (3×200 ml). The combined extracts are dried ($Na_2SO_4$), filtered and the solvent is evaporated off under reduced pressure to yield the crude product. This is purified by chromatography (silica gel, 10% acetone in hexane) and recrystallized from diethyl ether-pentane to give the title compound, m.p. 92°–93° C.

e. 6-Bromo-2,2,7-trimethyl-2H-1-benzopyran

A stirred solution of the product of step d (27.1 g) in dry toluene (300 ml) is treated with p-toluenesulphonic acid (1.15 g) and heated under reflux for 2 h with water formed being removed via a Dean-Stark apparatus. The cooled solution is washed with aqueous sodium carbonate (100 ml, 2M), dried ($Na_2SO_4$), filtered and the solvent is evaporated off under reduced pressure to yield the crude product. This is purified by chromatography (silica gel, hexane) to give the title compound as an oil.

f. 6-(2-methylpyridin-4-yl)-2,2,7-trimethyl-2H-1-benzopyran

A solution of the product of step e (7.60 g) in dry tetrahydrofuran (30 ml) is added over 15 min. to a stirred mixture of magnesium turnings (0.85 g) and iodine (0.06 g) in dry tetrahydrofuran (25 ml) at 45° C. under an argon atmosphere. The mixture is heated under reflux for 3 h, cooled to 5° C., treated with bis-(triphenylphosphine)nickel (II) chloride (0.32 g) and a solution of 4-bromopicoline (4.8 g) in dry tetrahydrofuran (50 ml) and stirred at room temperature for 18 h. The mixture is treated with HCl (140 ml, 1M) and extracted with diethyl ether (2×60 ml). The combined ether extracts are washed with HCl. The combined acid solutions are basified to pH 10 with $K_2CO_3$, extracted with diethyl ether (3×100 ml), dried ($Na_2SO_4$), filtered and the solvent is evaporated off under reduced pressure to yield the crude product. This is purified by chromatography (silica gel, 10% acetone in hexane) to give the title compound as an oil, having the following physical characteristics: $^1$H-NMR($\delta$-CDCl$_3$): 1.44 (s,6H), 2.21 (s,3H), 2.59 (s, 3H), 5.60 (d,1H), 6.31 (d,1H), 6.70 (s,1H), 6.82 (s,1H), 7.04 (dd,1H), 7.09 (d,1H) and 8.49 (d,1H).

A.4. Preparation of trans-(±)3-Bromo-3,4-dihydro-2,2-dimethyl-6-(2-methylpyridin-4-yl)-2H-1-benzopyran-4-ol N-Bromosuccinimide (2.20 g) is added in portions to a stirred solution of the product of Example A.3. (2.50 g) in dimethylsulphoxide (6 ml) and $H_2O$ (0.36 ml) at 0° C. After exothermic reaction has subsided, stirring is continued for an additional 1 h and the reaction is quenched with saturated aqueous $NH_4Cl$ (200 ml) and extracted with $CH_2Cl_2$ (3×100 ml). The combined extracts are dried ($Na_2SO_4$), filtered and the solvent is evaporated off under reduced pressure to yield the crude product. This is purified by chromatography (silica gel, 2% $C_2H_5OH$ in $CH_2Cl_2$) and recrystallized from $C_2H_5OH$-diethyl ether to give the title compound, m.p. 212°–214° C.

A.5. Preparation of (±)-4-(1a, 7b-Dihydro-2,2-dimethyl-2H-oxi-reno [c][1] benzopyran-6-yl)-2-methylpyridine A solution of the product of Example A.4. (3.5 g) in dry tetrahydrofuran (80 ml) is treated with NaH (0.90 g of a 55% dispersion in oil) and stirred at room temperature under argon for 1 h. The reaction is quenched with a saturated aqueous solution of $NH_4Cl$ (150 ml) and extracted with diethyl ether (3×100 ml). The combined extracts are dried ($Na_2SO_4$), filtered and the solvent is evaporated off under reduced pressure to give a residue which is purified by chromatography (silica gel, 2% $C_2H_5OH$ in $CH_2Cl_2$) to give the title compound as an oil having the following physical characteristics: $^1$H-NMR ($\delta$-d$^6$ DMSO): 1.23 (s,3H), 1.50 (s,3H), 2.52 (s,3H), 3.75 (d,1H), 4.14 (d,1H), 6.89 (d,1H), 7.47 (dd,1H), 7.56 (s,1H 7.19 (dd,1H), 7.96 (d,1H) and 8.47 (d,1H).

The following compounds of formula II in which $R_6$ and $R_7$ are each methyl and $R_1$, $R_2$ and $R_8$ have the significances indicated may be prepared analogously to Examples A4 and A5 above, but carrying out reaction by a one-pot procedure. This is done by diluting the mixture obtained subsequent to exothermic reaction and stirring according to Example A.4. with dioxan, treating with aqueous NaOH (0.6M) and stirring at room temperature for ca. 1 h further. Purification then proceeds analogously to Example A.5. following evaporation of dioxan. The starting materials are as shown in column 2 of the table. All products are obtained as the (±) racemate in the form of an oil.

| EX-AMPLE | STARTING MATERIAL FROM EXAMPLE | $R_1$ | $R_2$ | $R_8$ |
| --- | --- | --- | --- | --- |
| B5 | B3 | $C_2H_5$— | H | H |
| C5 | C3 | $CH_3$— | $CH_3$— | H |
| D5 | D3 | H | $CH_3$— | H |
| E5 | E3 | $nC_3H_7$— | H | H |
| F5 | F3 | $iC_4H_7$— | H | H |
| G5 | G3 | $HOCH_2$— | H | H |
| H5 | H3 | $CH_3OCH_2$— | H | H |
| I5 | I | $CH_3$— | H | $CH_3$— |

CHARACTERIZING DATA

B.5. $^1$HNMR ($\delta$-CDCl$_3$): 1.31 (s,3H), 1.37 (t,3H), 1.62 (s,3H), 2.89 (q,2H), 3.56 (d,1H), 3.99 (d,1H), 6.91 (d, 1H), 7.28 (dd,1H), 7.34 (m,1H), 7.54 (dd,1H) 7.63 (d,1H) and 8.54 (dd,1H).

C.5. $^1$H-NMR ($\delta$-CDCl$_3$): 1.32 (s,3H), 1.61 (s,3H), 2.20 (s,3H), 2.61 (s,3H), 3.54 (d,1H), 3.39 (d,1H), 6.87 (d,1H), 6.98 (d,1H), 7.17 (dd,1H), 7.26 (d,1H) and 8.32 (d,1H).

D.5. $^1$H-NMR ($\delta$-CDCl$_3$): 1.33 (s,3H), 1.62 (s,3H), 2.31 (s,3H), 3.55 (d,1H), 3.95 (d,1H), 6.89 (d,1H), 7.13 (d,1H), 7.23 (dd,1H), 7.31 (s,1H), 8.45 (d,1H) and 8.49 (s,1H).

E.5. $^1$H-NMR ($\delta$-CDCl$_3$): 1.01 (t,3H), 1.30 (s,3H), 1.62 (s,3H), 1.82 (sex,2H), 2.82 (t,2H), 3.54 (d,1H), 3.98 (d,1H), 6.91 (d,1H), 7.28 (dd, 1H), 7.32 (d, 1H), 7.53 (dd,1H), 7.63 (d,1H) and 8.54 (d,1H).

F.5. $^1$H-NMR ($\delta$-CDCl$_3$): 0.96 (d,6H), 1.30 (s,3H), 1.62 (s,3H), 2.15 (dt,1H), 2.70 (d,2H), 3.54 (d,1H), 3.93 (d,1H), 6.90 (d,1H), 7.22–7.30 (m,2H), 7.53 (dd,1H), 7.63 (d,1H) and 8.54 (d,1H).

G.5. $^1$H-NMR ($\delta$-CDCl$_3$): 1.31 (s,3H), 1.63 (s,3H), 3.55 (d,1H), 3.98 (d,1H), 4.83 (s,2H), 6.92 (d,1H), 7.35–7.45 (m,2H), 7.54 (dd,1H), 7.64 (d,1H) and 8.57 (d,1H).

I.5. $^1$H-NMR ($\delta$-CDCl$_3$): 1.29 (s,3H), 1.59 (s,3H), 2.21 (s, 3H), 2.60 (s,3H), 3.50 (d,1H), 3.89 (d,1H), 6.74 (s,1H), 7.04 (dd,1H), 7.10 (d,1H), 7.18 (s,1H) and 8.50 (d,1H).

A.5' preparation of (−)-(3S, 4S)-4-(1a, 7b-dihydro-2,2-dimethyl-2H-oxireno [c][1]benzopyran-6-yl)-2-methylpyridine A.5.'a [1R-[1α(3R, 4S),4β]- and [1R-[1a(3S, 4R), 4β]-α-methoxybenzene acetic acid, 3-bromo-3,4-dihydro-2,2-dimethyl-6-(2-methylpyridin-4-yl)-2H-1-benzopyran-4-yl, ester.

A solution of the product of Example A.4. (9.80 g), (−)-(R)-α-methoxyphenylacetic acid (5.65 g) and 4-dimethylaminopyridine (0.45 g) in dry $CH_2Cl_2$ (330 ml), is treated with N,N-dicyclohexylcarbodiimide (6.81 g) and stirred for 90 min at room-temperature. The mixture is filtered and the solvent evaporated off under reduced pressure to give a crude mixture of diastereoisomers which is purified by chromatography (silica gel, 5% acetone in $CH_2Cl_2$) to yield a less polar product (A) which is recrystallized from acetone-pentane to give the [1R-[1α(3R, 4S), 4β] isomer of the title compound, m.p. 137°–138° C., $[α]_D^{20}=-75.4°$ (c=0.955, $C_2H_5OH$) and, as a more polar product, (B) the [1R-[1α(3S, 4R), 4β] isomer of the title compound as an oil, $[α]_D^{20}=-22°$ (c=0.975, $C_2H_5OH$).

A.5'.b (−)-(3S, 4S)-4-(1a, 7.b,Dihydro-2,2-dimethyl-2H-oxireno [c][1]benzopyran-6-yl)-2-methylpyridine A solution of [1R- [1α(3R, 4S), 4β] isomer product of step (A.5'.a) (3.16 g) in dioxan (75 ml) at 20° C. is treated with aqueous NaOH (45 ml of 0.58 m) and stirred for 10 min at 20° C. The dioxan is evaporated. off under reduced pressure and the residue treated with $H_2O$ (100 ml) and extracted with $CH_2Cl_2$ (3×100 ml). The combined extracts are dried ($Na_2SO_4$), filtered and the solvent is evaporated off under reduced pressure to give a residue which is purified by column chromatography (silica gel, 5% $C_2H_5OH$ in $CH_2Cl_2$) to give the title compound in pure or substantially pure enantiomeric form as a colorless oil, $[α]_D^{20}=-72°$ (c=1.125, $C_2H_5OH$).

A.6'. Preparation of (+)-(3S, 4R)-4-amino-3,4-dihydro-2,2-dimethyl-6-(2-methylpyridin-4-yl)-2H-1-benzopyran-3-ol A solution of the product of Example A.5' (0.64 g) is treated with saturated $NH_3$ in $C_2H_5OH$ (15 ml) and heated at 80° C. in an autoclave for 15 hours. The solvent is evaporated off under reduced pressure to yield the crude product which is purified by chromatography (silica gel, 5% $C_2H_5OH$ in $CH_2Cl_2$) to give the title compound as a foam: $[α]^{20}_D=+100°$, (c=1.00, $C_2H_5OH$).

The following compounds of formula IV in which $R_4$ is H, $R_5$ is hydroxy, $R_6$ and $R_7$ are each methyl and $R_1$, $R_2$ and $R_8$ have the meanings shown may be produced analogously from the indicated starting material. All compounds listed in this table are in the form of the trans racemate and, except for the product of Example B6, are obtained as an oil.

| EXAMPLE | $R_1$ | $R_2$ | $R_8$ | STARTING MATERIAL ACCORDING TO EXAMPLE |
|---|---|---|---|---|
| A6 | $CH_3$— | H | H | A5 |
| B6 | $C_2H_5$— | H | H | B5 |
| C6 | $CH_3$— | $CH_3$— | H | C5 |
| E6 | $nC_3H_7$— | H | H | E5 |
| F6 | $iC_4H_9$— | H | H | F5 |
| H6 | $CH_3OCH_2$— | $CH_3$ | H | H5 |
| I6 | $CH_3$— | H | $CH_3$ | I5 |

PHYSICAL DATA

A.6. $^1$H-NMR ($δ^6$-DMSO): 1.12 (s,3H), 1.38 (s,3H), 2.06 (broad, 2H), 2.50 (s,3H), 3.23 (dd,1H), 3.59 (d,1H), 5.47 (d,1H), 6.81 (d,1H), 7.43 (dd,1H), 7.51 (s,1H), 7.55 (dd,1H), 7.99 (m,1H) and 8.44 (d,1H)

B.6. M.P.=140°–141° C.

C.6. $^1$H-NMR (δ-$CDCl_3$): 1.27 (s,3H), 1.54 (s,3H), 2.15 (s,3H), 2.2–2.5 (br.s,3H), 2.57 (s,3H), 3.41 (d,1H), 3.71 (d,1H), 6.85 (d,1H), 6.99 (d,1H), 7.10 (dd,1H), 7.31 (dd,1H) and 8.31 (d,1H).

E.6. $^1$H-NMR (δ-$CDCl_3$): 1.00 (t,3H), 1.27 (s,3H), 1.55 (s,3H), 1.80 (s,2H), 2.0–2.4 (br.s,3H), 2.80 (t,2H), 3.41 (d,1H), 3.74 (d, 1H), 6.89 (d,1H), 7.25–7.36 (m,2H), 7.47 (dd,1H), 7.70 (d,1H) and 8.51 (d,1H).

F.6. $^1$H-NMR (δ-DMSO): 0.90 (d,6H), 1.13 (s,3H), 1.41 (s,3H), 2.0–2.2 (br.s,2H), 2.09 (dt,1H), 2.65 (d,2H), 3.24 (dd,1H), 3.63 (d,1H), 5.45 (br.d,1H), 6.84 (d,1H), 7.48 (m,2H), 7.58 (dd,1H), 8.00 (d,1H) and 8.4 6 (d,1H).

I.6. $^1$H-NMR (δ-$CDCl_3$): 1.24 (s,3H), 1.53 (s,3H), 2.1–2.4 (br.s,3H), 2.20 (s,3H), 2.60 (s,3H), 3.38 (d,1H), 3.67 (d,1H), 6.73 (s,1H), 7.05 (d,1H), 7.10 (s,1H), 7.21 (s,1H) and 8.49 (d,1H).

Benzopyrans and dihydrobenzopyrans as defined under 1. above, for example compounds of formula I as hereinbefore defined, and their N-oxides, and physiologically-hydrolyzable and -acceptable esters thereof, as well as pharmaceutically acceptable acid addition and quarternary ammonium salts of said benzopyrans/dihydrobenzopyrans/N-oxides/esters, (hereinafter collectively AGENTS OF THE INVENTION) are useful as pharmaceuticals.

AGENTS OF THE INVENTION possess smooth muscle relaxant activity and exhibit potassium channel opening activity in relation to the plasmalemma membrane as demonstrated by their influence at concentrations in the region of 1 to 500 nM on tension in, and of $Rb^+$ efflux from, various smooth muscle preparations in accordance with or analogously to the methods described in Quast, Brit. J. Pharmac., 91, 569–578 (1987). AGENTS OF THE INVENTION are thereby characterized as $K^+$ channel opening agents.

AGENTS OF THE INVENTION are accordingly useful for the treatment of conditions or disorders for which therapy employing a $K^+$ channel opening agent is indicated. Therapeutic utility as $K^+$ channel opening agents may further be demonstrated in standard pharmacological tests, e.g. of cardio-vascular activity, in vitro or in vivo. Thus influence on blood-pressure may be demonstrated in the anaesthetized, cannulated normotensive rat following intra duodenal administration 1 hr post cannulation. Anti-ischemic activity may be demonstrated in accordance with the methods described in Hof et al., Circ. Res., 62, 679 (1988). AGENTS OF THE INVENTION exhibit hypotensive activity in the former test method at threshold doses of from about 0.03 to about 1.0 mg/kg i.d. and anti-ischemic activity in the latter test method at doses of from about 0.001 to about 0.03 mg/kg i.v.

AGENTS OF THE INVENTION are accordingly useful, e.g. as smooth muscle relaxants, in particular for use as vasodilating agents, for example for the treatment of hypertension or chronic cardiac-insufficiency. They are further useful as anti-ischemic and anti-vasospastic agents, e.g. for use in the treatment of disturbed blood supply, for example to the heart, skeletal muscle or brain. They are thus useful e.g. for the treatment of angina pectoris, myocardial ischemia or myocardial infarction; as antifibrillatory agents; for the treatment of disorders of peripheral circulation, e.g. claudicatio intermittens, Morbus Raynaud or venous ulcer; as well as for the treatment, including prophylaxis, of cerebral ischemia, senile dementia, stroke, subarachnoidal hemorrhage and other related or consequential diseases or disorders.

AGENTS OF THE INVENTION are yet further indicated for use as gastro-intestinal, uterine and urinary tract antispastic agents, e.g. for the treatment of duodenal or peptic ulcer, irritable colon, diverticulitis, danger of miscarriage following premature labor and urinary incontinence.

AGENTS OF THE INVENTION are yet further indicated for use as hair-growth stimulating agents, e.g. for the treatment of hair loss due to ageing, e.g. male alopecia or pattern baldness, or disease-related hair loss for example consequent to infection or disturbance of the immune system.

Suitable dosages for such use will of course vary, e.g. depending on the particular condition to be treated, the particular AGENT OF THE INVENTION employed, the mode of administration and the effect desired. In general, however, a suitable oral daily dosage, e.g. for anti-hypertensive uses, will be from about 0.03 to about 2.0 mg/kg and for, e.g. anti-ischemic uses, from about 0.015 to about 0.3 mg/kg. For larger mammals, e.g. humans, an indicated oral daily dosage will thus be from about 2 to about 150 mg for anti-hypertensive uses, or from about 1 to about 20 mg for anti-ischemic uses, administered once or in divided doses 2× daily. Oral dosage forms for use in the above indications will thus suitably comprise from about 0.5 or 1.0 to about 20 or 150 mg AGENT OF THE INVENTION together with a pharmaceutically acceptable diluent or carrier therefor.

For use as hair-growth stimulating agents, AGENTS OF THE INVENTION will appropriately be applied topically, e.g. in an appropriate cream, gel or emulsion base or the like as known in the art.

More importantly, it has in accordance with the present invention been found that AGENTS OF THE INVENTION possess bronchodilator activity and reduce or reverse airways hyperreactivity. These activities may also be demonstrated in pharmaceutical test models in vivo and in vitro, for example as follows:

TEST 1. BRONCHODILATOR ACTIVITY 1.1 In the Guinea-Pig

Guinea-pigs (Dunkin-Hartley, male, 400–600 g) are anaesthetized with phenobarbital (100 mg/kg i.p.) and pentobarbital (30 mg/kg i.p.) and paralyzed with gallamine (8 mg/kg i.m.) and ventilated with a mixture of air and oxygen (45:55, v/v). Animals are ventilated via a tracheal cannula (10 ml/kg, 1 Hz). Blood pressure and heart rate are recorded from the carotid artery. Ventilation is monitored by a flow transducer. When making measurements of flow, coincident pressure changes in the thorax are monitored directly via an intrathoracic trochar, permitting display of differential pressure relative to the trachea. From this information resistance and compliance are calculated at each inspiration.

Intravenous infusion of bombesin (100 ng/kg/h) induces sustained bronchospasm. Capacity of test substance to reverse response when administered by the intratracheal route serves as a measure of efficacy in reversing established bronchospasm. The bronchodilator response is taken as the percentage reduction of the maximal response to bombesin, measured at regular intervals.

In the above test model, AGENTS OF THE INVENTION effect dose related abrogation of bronchospasm at dosages of from about 0.001 to about 1.0 mg/kg.

1.2 In the Rhesus Monkey

Rhesus monkeys (male and female, body wt 6.8–11.8 kg) known to be normal responders to methacholine (MeCH), are anaesthetized (initial: ketamine 20 mg/kg i.m., maintenance: thiopental 8 mg/kg/h i.v.). A cuffed pediatric endotracheal tube (5.0 cm) is then introduced into the trachea (xylocaine: topical administration at the epiglottus) and basal lung resistance measured.

Following these maneuvers, 2 ml xylocaine (1% w/v solution) is administered at the carina with a pediatric fibreoptic bronchoscope. 10 minutes later, lung resistance is again measured. Xylocaine has no effect on base-line resistance. Test substance is administered in a similar manner to xylocaine pretreatment, in a lactose vehicle suspension (1 mg/ml, 1 ml delivered volume) in a cumulative manner at 30 min. intervals. At the 15 minute time point, a single MeCH challenge (0.6 to 2.5 mg/ml solution, estimated to produce approximately a 50–100% change from baseline) is performed and the % inhibition calculated from the response after vehicle administration.

AGENTS OF THE INVENTION produce potent, dose-dependent bronchodilator effect in the above test method at dosages of from about 10 ng/kg to about 10 µg/kg.

TEST 2. SUPPRESSION OF AIRWAYS HYPERREACTIVITY 2.1 PAF-induced hyperreactivity

Guinea-pigs are prepared for recording of lung function as described under Test 1.1 above. Intravenous injection of histamine (1.8–3.2 µg/kg) establishes airways sensitivity to spasmogen. Following infusion of PAF (platelet activating factor) over 1 hour (total dose 600 ng/kg), repeated injection of histamine reveals development of airways hyperreactivity, which can conveniently be expressed as the paired difference between the response amplitude before and after PAF exposure.

On administration of AGENTS OF THE INVENTION intratracheally after PAF exposure at dosages of from about 0.1 to about 100 µg/kg, reversal of airways hyperreactivity induction is observed.

2.2 Immune-complex-induced hyperreactivity Guinea pigs are prepared for recording of lung-function as described under Test 1.1 above. An allergic reaction is initiated by intravenous injection of preformed immune-complexes (prepared by adding 30 µg of bovine gamma globulin in 0.05 ml of saline to 0.05 ml of guinea pig anti-bovine gamma globulin anti-serum) at regular (10 min) intervals for 30 min. Intravenous injections of histamine (1.0–3.2 µg/kg at 10 min intervals) are used to define the sensitivity of the airways prior to and following the last exposure to immune-complex. Airways hyperreactivity is expressed as the paired difference for the maximal value of lung resistance in response to histamine before and after repeated injection of immune-complex. Test compounds are administered intratracheally.

Induced airways hyperreactivity is significantly reduced in the above test method by prior treatment with AGENTS OF THE INVENTION, at dosages of from about 10 ng/kg to about 10.0 µg/kg.

AGENTS OF THE INVENTION are accordingly useful in particular as bronchodilator agents and as agents for the therapy of airways hyperreactivity e.g. as agents for the symptomatic as well as prophylactic treatment of obstructive or inflammatory airways disease, in particular asthma. As bronchodilator agents, AGENTS OF THE INVENTION may be employed, in particular as rescue therapy, to treat bronchoconstrictor attack, e.g. in asthma. In addition, by continued administration, AGENTS OF THE INVENTION may be used for the control, restriction or reversal of airways hyperreactivity or to provide advance protection against recurrence of bronchoconstrictor attack consequential to obstructive or inflammatory airways disease, in particular asthma. The words "treatment" and "treating" as used throughout the present specification and claims in relation to use of AGENTS OF THE INVENTION for the treatment of obstructive or inflammatory airways disease, in particular asthma, are accordingly to be understood as embracing both prophylactic as well as symptomatic (i.e. bronchodilator) modes of therapy, unless otherwise specified.

In accordance with the foregoing the present invention also provides:

4. A method for the treatment of any disease or condition herein specified; in particular
4.a A method for the treatment of obstructive or inflammatory airways disease; including
4.a.1 A method for the symptomatic treatment of inflammatory or obstructive airways disease, e.g. of effecting bronchodilatation; or
4.a.2 A method for the prophylactic treatment of inflammatory or obstructive airways disease, e.g. for the treatment of airways hyperreactivity;
in a subject in need thereof, which method comprises administering to said subject an effective amount of an AGENT OF THE INVENTION:
or, in the alternative:
5. An AGENT OF THE INVENTION for use as a pharmaceutical, e.g. for use in the treatment of any disease or condition as herein specified, in particular for use in the treatment of obstructive or inflammatory airways disease, e.g. as indicated under 4.a.1 or 4.a.2 above; or
6. A pharmaceutical composition comprising an AGENT OF THE INVENTION, or use of an AGENT OF THE INVENTION for use in the preparation of a pharmaceutical composition, for use in the treatment of any disease or condition herein specified, in particular for use as set forth under 5 above.

Inflammatory or obstructive airways diseases to which the present invention is applicable include asthma of whatever type or genesis including both intrinsic and, especially, extrinsic asthma. They are useful for the treatment of allergic asthma, whether atopic, (i.e. IgE-mediated) or non-atopic, as well as, for example, bronchitic asthma, exercise induced asthma, occupational asthma, asthma induced following bacterial infection and other non-allergic asthmas. Treatment of asthma is also to be understood as embracing treatment of subjects, e.g. of less than 4 or 5 years of age, exhibiting wheezing symptoms, in particular at night, and diagnosed or diagnosable as "wheezy infants", an established patient category of major medical concern and now more correctly identified as incipient or early-phase asthmatics. (For convenience this particular asthmatic condition is referred to as "wheezy-infant syndrome".)

Prophylactic efficacy in the treatment of asthma will be evidenced by reduced frequency or severity of symptomatic attack, e.g. of acute asthmatic or bronchoconstrictor attack.

It may further be evidenced by reduced requirement for other, symptomatic therapy, i.e. therapy for or intended to restrict or abort symptomatic attack when it occurs, for example anti-inflammatory (e.g. corticosteroid) or bronchodilatory (e.g. $\beta_2$ adrenergic) therapy.

Prophylactic benefit in asthma may in particular be apparent in subjects prone to "morning dipping". "Morning dipping" is a recognized asthmatic syndrome, common to a substantial percentage of asthmatics and characterized by asthma attack, e.g. between the hours of about 4 to 6 am, i.e. at a time normally substantially distant from any previously administered symptomatic asthma therapy, Inflammatory or obstructive airways diseases to which the present invention is applicable also include pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, ptilosis, siderosis, silicosis, tabacosis and, in particular, byssinosis.

Further inflammatory or obstructive airways diseases and conditions to which the present invention is applicable include adult respiratory distress syndrome (ARDS), chronic obstructive pulmonary or airways disease (COPD or COAD), and bronchitis, as well as exacerbation of airways hyperreactivity consequent to other drug therapy, in particular other inhaled drug therapy, e.g. $\beta$-agonist bronchodilator therapy, including in particular usage of AGENTS OF THE INVENTION as bronchodilators for the treatment of chronic or acute airways obstruction as well as dyspnea, associated with any of the said diseases or conditions.

For use in the treatment of inflammatory or obstructive airways disease AGENT OF THE INVENTION may be administered by any conventional route, in particular enterally, e.g. orally, for example in the form of tablets or capsules, or parenterally, e.g. in the form of injectable solutions or suspensions. Preferably however they will be administered by the pulmonary route, e.g. by inhalation from an appropriate nebulizer, inhaler or like device as known in the art.

Dosages employed in the treatment of inflammatory or obstructive airways disease will of course vary depending, e.g. on the particular condition to be treated, the particular AGENT OF THE INVENTION employed, the mode of administration and the effect desired.

In general however, for pulmonary administration for larger mammals, e.g. humans, a suitable daily dosage delivered to the lungs will be of the order of from about 0.1 µg to about 100 µg, in particular from about 1.0 µg to about 50.0 µg, suitably administered from an inhaler device with administration effected once or from 2 to 4× daily, in a series of from 1 to 4 puffs at each administration.

For oral administration a suitable daily dosage will generally be of the order of from about 0.1 to about 30 µg/kg. A suitable oral daily dosage for larger mammals, e.g. humans, will thus be of the order of from about 7 µg to about 2.1 mg, administered in a single dose, in divided doses administered from 2 to 4× daily, or in sustained release form. Oral unit dosage forms for such use will thus suitably comprise from about 1.75 µg to about 2.1 mg of an AGENT OF THE INVENTION together with a pharmaceutically acceptable diluent or carrier therefor.

In this connection it is in particular to be noted that AGENTS OF THE INVENTION are generally active as bronchodilators or as agents for the treatment of airways hyperreactivity at dosages, in particular inhaled dosages, at which cardiovascular effects which would be undesirable in relation to such therapy, e.g. hypotensive/tachycardial effect are non-significant or within acceptable limits of tolerability in relation to the therapy practiced.

In accordance with the foregoing the present invention also provides:

7. A pharmaceutical composition comprising an AGENT OF THE INVENTION together with a pharmaceutically acceptable diluent or carrier therefor.

Such compositions may be manufactured in conventional manner, e.g. for pulmonary administration by compounding an AGENT OF THE INVENTION in finely divided disperse particulate form, e.g. together with finely divided lactose as a carrier/diluent to form an inhalable powder.

As previously indicated, therapeutic dosage requirements in practicing the present invention will vary depending on a variety of factors. Dosaging for any particular AGENT OF THE INVENTION will also depend on its relative potency of action. For the preferred AGENT OF THE INVENTION, namely the product of Example 1 in pure or substantially pure (3S, 4R) enantiomeric form an established $ID_{50}$ in one test run carried out in accordance with Test 1.1 hereinbefore is 0.02 mg/kg, i.t. An established $ID_{50}$ in the same test method for the known inhaled bronchodilator drug salbutamol [$\alpha^1$-[[(1,1-Dimethyl ethyl)amino]-methyl]-4-hydroxy-1,3-benzenemethanol] is 0.001 mg/kg, i.t. Appropriate dosages of the Example 1 compound for administration by inhalation, e.g. for bronchodilator effect in asthma therapy, will thus be anticipated to be ca. 20× those conventionally required using Salbutamol.

I claim:

1. A compound having the formula

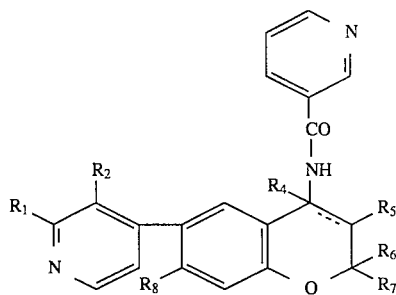

wherein $R_1$ and $R_2$ are, independently, hydrogen, $C_{1-5}$alkyl, $C_{1-5}$ hydroxyalkyl or $C_{1-5}$(alkoxyalkyl), whereby at least one of $R_1$ and $R_2$ is other than hydrogen, $R_4$ is hydrogen and $R_5$ is hydroxy in the trans position with respect to the pyridine carboxamido moiety, or $R_4$ and $R_5$ together represent an additional bond as indicated by the dotted line, $R_6$ and $R_7$ are, independently, $C_{1-5}$alkyl, and $R_8$ is hydrogen or $C_{1-5}$alkyl, or an N-oxide thereof, or an acid addition or quaternary ammonium salt of such a compound or N-oxide.

2. A compound according to claim 1 wherein $R_4$ is hydrogen, $R_5$ is hydroxy in the trans position with respect to the pyridine carboxamido moiety, $R_6$ and $R_7$ are each methyl and a) $R_1$ is methyl, ethyl, n-propyl, i-butyl or methoxymethyl and $R_2$ and $R_8$ are each hydrogen, or b) $R_1$ and $R_2$ are each methyl and $R_8$ is hydrogen, or c) $R_1$ and $R_8$ are each methyl and $R_2$ is hydrogen;

or an N-oxide thereof, or an acid addition or quaternary ammonium salt of such a compound or N-oxide.

3. A compound according to claim 1 wherein $R_4$ is hydrogen and $R_5$ is hydroxy in the trans position with respect to the pyridine carboxamido moiety, and $R_1$, $R_2$, $R_6$, $R_7$ and $R_8$ are as defined in claim 1, or an N-oxide thereof, or an acid addition or quaternary ammonium salt of such a compound or N-oxide, which compound is in (3S, 4R) enantiomeric form.

4. The compound of claim 2 which is (+)-(3S, 4R)-[3,4-dihydro-2,2-dimethyl-3-hydroxy-6-(2-methylpyridin-4-yl)-2H-1-benzopyran]-3-pyridinecarboxamide, or an N-oxide thereof or an acid addition or quaternary ammonium salt of said compound or N-oxide.

5. The compound of claim 4 which is in free base form.

6. A compound of claim 1 which is in free base form.

7. A compound of claim 1 which is in free base or pharmaceutically acceptable acid addition salt form.

8. A compound of claim 2 which is in free base form.

9. A compound of claim 2 which is in free base or pharmaceutically acceptable acid addition salt form.

10. A compound of claim 3 which is in free base form.

11. A compound of claim 3 which is in free base or pharmaceutically acceptable acid addition salt form.

12. A 2,2-di($C_{1-5}$alkyl)-, or trans-2,2-di($C_{1-5}$alkyl)-3,4-dihydro-3-hydroxy- -6-(pyridin-4-yl)-2H-1-benzopyran having a pyridine carboxamido moiety in the 4-position and wherein the pyridin-4-yl group is substituted in the 2- and/or 3-position by one or two members selected from the group consisting of $C_{1-5}$alkyl, $C_{1-5}$ hydroxyalkyl and $C_{1-5}$(alkoxyalkyl), or an N-oxide thereof, or an acid addition or quaternary ammonium salt of such a benzopyran or N-oxide.

13. A compound of claim 12 which is in free base form.

14. A compound of claim 12 which is in free base or pharmaceutically acceptable acid addition salt form.

15. A pharmaceutical composition comprising a pharmaceutically acceptable carrier or diluent and a therapeutically effective amount of a benzopyran of claim 12 or an N-oxide thereof, or a pharmaceutically acceptable acid addition or quaternary ammonium salt of such a benzopyran or N-oxide.

16. A method of treating obstructive or inflammatory airways disease comprising administering to a subject in need of such treatment a therapeutically effective amount of a benzopyran of claim 12 or an N-oxide thereof, or a pharmaceutically acceptable acid addition or quaternary ammonium salt of such a benzopyran or N-oxide.

17. A composition according to claim 15 wherein the compound is present in free base form.

18. A composition according to claim 15 wherein the compound is present in free base or pharmaceutically acceptable acid addition salt form.

19. A method according to claim 16 wherein the compound is administered in free base form.

20. A method according to claim 16 wherein the compound is administered in free base or pharmaceutically acceptable acid addition salt form.

* * * * *